United States Patent    (10) Patent No.: US 11,604,156 B2
Chen et al.    (45) Date of Patent: Mar. 14, 2023

(54) METHOD AND SYSTEM FOR MULTI-SENSOR GAS DETECTION

(71) Applicant: Carrier Corporation, Palm Beach Gardens, FL (US)

(72) Inventors: Lei Chen, South Windsor, CT (US); Marcin Piech, East Hampton, CT (US)

(73) Assignee: CARRIER CORPORATION, Palm Beach Gardens, FL (US)

( * ) Notice: Subject to any disclaimer, the term of this patent is extended or adjusted under 35 U.S.C. 154(b) by 699 days.

(21) Appl. No.: 16/613,084

(22) PCT Filed: May 11, 2018

(86) PCT No.: PCT/US2018/032413
§ 371 (c)(1),
(2) Date: Nov. 12, 2019

(87) PCT Pub. No.: WO2018/209296
PCT Pub. Date: Nov. 15, 2018

(65) Prior Publication Data
US 2020/0166470 A1    May 28, 2020

Related U.S. Application Data

(60) Provisional application No. 62/505,652, filed on May 12, 2017.

(51) Int. Cl.
*G01K 13/00* (2021.01)
*G01N 27/16* (2006.01)
(Continued)

(52) U.S. Cl.
CPC .............. *G01N 27/16* (2013.01); *F24F 11/36* (2018.01); *G01N 33/0031* (2013.01)

(58) Field of Classification Search
CPC ...... G01N 27/16; G01N 33/0031; F24F 11/36
(Continued)

(56) References Cited

U.S. PATENT DOCUMENTS 4,233,817 A    11/1980  Toth
6,071,476 A *  6/2000  Young ................... G01N 25/30
                                                        422/51
(Continued)

FOREIGN PATENT DOCUMENTS

EP    0293255 A2    11/1988
GB    2248940 A      4/1992
(Continued)

OTHER PUBLICATIONS

International Search Report Issued in International Application No. PCT/US2018/032413 dated Aug. 21, 2018; 6 Pages.
(Continued)

*Primary Examiner* — Davis D Hwu
(74) *Attorney, Agent, or Firm* — Cantor Colburn LLP (57) ABSTRACT

Methods and systems are disclosed in which metal oxide composition electrical resistance is measured in a plurality of sensors to detect flammable or reducing compounds wherein at least one of the plurality of sensors is operated at a temperature or includes a metal oxide composition that is different than a respective temperature or metal oxide composition of another of the plurality of sensors.

20 Claims, 6 Drawing Sheets

(51) Int. Cl.
*F24F 11/36* (2018.01)
*G01N 33/00* (2006.01)

(58) Field of Classification Search
USPC .......................................................... 62/129
See application file for complete search history.

(56) References Cited

U.S. PATENT DOCUMENTS

| | | |
|---|---|---|
| 6,244,096 B1 | 6/2001 | Lewis et al. |
| 6,631,333 B1 | 10/2003 | Lewis et al. |
| 6,890,715 B1 | 5/2005 | Lewis et al. |
| 6,912,860 B2 | 7/2005 | Zima et al. |
| 7,122,152 B2 | 10/2006 | Lewis et al. |
| 7,171,312 B2 | 1/2007 | Steinthal et al. |
| 7,477,993 B2 | 1/2009 | Sunshine et al. |
| 8,070,355 B2 | 12/2011 | Minor et al. |
| 8,152,991 B2 | 4/2012 | Briman et al. |
| 8,394,330 B1 | 3/2013 | Lewis et al. |
| 9,182,366 B2 | 11/2015 | Izawa et al. |
| 2011/0021894 A1 | 1/2011 | Mohanty et al. |
| 2011/0112814 A1 | 5/2011 | Clark |
| 2012/0283540 A1 | 11/2012 | Broggemann |

FOREIGN PATENT DOCUMENTS

| | | |
|---|---|---|
| JP | 2014224612 A | 12/2014 |
| WO | 8501351 A1 | 3/1985 |
| WO | 9940423 A1 | 8/1999 |
| WO | 2016166126 A1 | 10/2016 |

OTHER PUBLICATIONS

Written Opinion Issued in International Application No. PCT/US2018/032413 dated Aug. 21, 2018; 10 Pages.

* cited by examiner

METHOD AND SYSTEM FOR MULTI-SENSOR GAS DETECTION

CROSS-REFERENCE TO RELATED APPLICATIONS

This application is the national stage of PCT/US2018/032413 filed May 11, 2018, which claims priority to U.S. Provisional Application No. 62/505,652 filed May 12, 2017, the disclosure of which is incorporated herein by reference in their entirety.

BACKGROUND

Gas sensors have been used in various applications such as process monitoring and control and safety monitoring. As the compounds can also be flammable or explosive, gas detection sensors have also been used for leak detection where such compounds are used or manufactured. Various types of sensors have been used or proposed, including but not limited to metal oxide semiconductor (MOS) sensors, non-dispersive infrared detector (NDIR) sensors, pellistor (pelletized resistor) sensors, high-temperature solid electrolytes that are permeable to oxygen ions, and electrochemical cells.

The above types of sensors have been used with varying degrees of success in the industrial or laboratory settings where they have been employed. However, many such sensors have limitations that can impact their effectiveness in demanding new and existing applications. For example, pellistor sensors are prone to false alarms due to cross-sensitivity. NDIR sensors have been used in low-volume applications, but can be difficult and expensive to manufacture to commercial tolerances. Electrochemical sensors rely on redox reactions involving tested gas components at electrodes separated by an electrolyte that produce or affect electrical current in a circuit connecting the electrodes. However, solid state electrochemical sensors can be difficult to implement for some materials. For example, solid state electrochemical sensors testing for combustible hydrocarbons may utilize solid electrolytes formed from ceramics such as perovskite, which can require high temperatures (typically in excess of 500° C.) that render them impractical for many applications. Some electrochemical sensors that operate at lower temperatures (e.g., carbon monoxide sensors, hydrogen sulfide sensors) require the presence of water at the electrode/electrolyte interface for the electrochemical redox reactions, which can render them impractical for many applications.

MOS sensors rely on interaction between gas test components such as hydrogen sulfide or hydrocarbons with adsorbed oxygen on the metal oxide semiconductor surface. In the absence of the gas test components, the metal oxide semiconductor adsorbs atmospheric oxygen at the surface, and this adsorbed oxygen captures free electrons from the metal oxide semiconductor material, resulting in a measurable level of base resistance of the semiconductor at a relatively high level. Upon exposure to reducing or combustible gas test components such as hydrocarbons or hydrofluorocarbons (HFCs), the gas test component interacts with the adsorbed oxygen, causing it to release free electrons back to the semiconductor material, resulting in a measurable decrease in resistance that can be correlated with a measured level of test gas component.

In the HVAC/R industry, more environmentally friendly refrigerants are being developed and used to replace refrigerants with high global warming potentials (GWP) such as R134A and R410A. Many of the low GWP refrigerants are flammable (A3 refrigerants such as R290 i.e. propane) or mildly flammable (A2L refrigerants such as R32, R1234ze etc.). Leak detection sensors have been proposed to address potential fire hazards from flammable refrigerants in interior building spaces. Conventional MOS sensors have been considered as a low-cost option for such applications. However, it has been shown that MOS sensors can be deactivated due to exposure to certain volatile chemicals that can be present in commercial and residential environment. Both temporary and permanent poisoning associated with those volatile compounds can occur. U.S. Pat. No. 9,182,366 discloses a method of rapidly cycling the temperature of the sensing element of a micro-electromechanical system (MEMS) MOS sensor between high and low temperatures to vaporize contaminants. In this method, an embedded heater would experience thermal cycles all the time, which can compromise the lifetime of the sensor. It is also unclear whether conventional non-MEMS could even sustain the rapid thermal cycling at all. In addition, it is unknown whether a sensor is still operational if degradation or accidental poisoning has substantially shortened the lifetime of the sensor. For a device used for safety monitoring, the lack of notification of unpredictable failures can be a significant disadvantage. US20020168772A1 discloses a method to diagnose whether a MOS sensor has been poisoned by modulating the temperature of the same sensing element and comparing its resistance changes. This method can temporarily interrupt the monitoring function when the diagnostic procedure is performed, and is therefore prone to the risk of being not available for detecting hazardous events during the sensor deployment.

Additionally, state-of-the-art MOS sensors can reach the end of life in 3 to 7 years in a benign environment even without deleterious chemicals, which can still be short of system requirements such as for HVAC systems. The use of a single sensing element for both primary monitoring and poisoning diagnostics can be further problematic due to the non-instantaneous thermal response when heater power is altered between diagnostics and normal operation modes.

BRIEF DESCRIPTION

According to some embodiments of this disclosure, a method for monitoring for flammable or reducing compounds comprises measuring metal oxide semiconductor composition electrical resistance in a plurality of sensors wherein a first sensor is operated at a first operating temperature for primary monitoring for flammable compounds. A second sensor is operated at a second temperature lower than the first temperature and above a temperature at which water vapor condensation can occur.

According to some embodiments, a monitoring system for flammable or reducing compounds comprises a plurality of sensors disposed in communication with a gas being monitored. The sensors individually comprise a metal oxide semiconductor composition, a resistance measurement device, and a heater. The system also includes a controller configured to operate the plurality of sensors. The controller and the heaters of the plurality of sensors are configured to operate a first sensor at a first operating temperature for primary monitoring for flammable compounds. The controller and the heaters of the plurality of sensors are configured to operate a second sensor at a second temperature lower than the first temperature and above a temperature at which water vapor condensation can occur.

According to any of the above embodiments, the gas being monitored can be flowing through a conduit, and the first and second sensors are disposed in the conduit with the second sensor downstream from the first sensor with respect to a direction of gas flow through the conduit.

According to some embodiments, an air conditioning system includes a first heat exchanger. The first heat exchanger comprises a conditioned air flow path on a first side of the heat exchanger, and a refrigerant flow path comprising a flammable refrigerant on a second side of the heat exchanger in thermal communication with the first thermal side. An enclosed fluid flow path comprising the flammable refrigerant connects the refrigerant flow path of the first heat exchanger with a second heat exchanger in thermal communication with an external heat source or heat sink. A plurality of sensors are disposed in an air space around the first heat exchanger or the enclosed fluid flow path. The sensors individually comprise a metal oxide semiconductor composition, a resistance measurement device, and a heater. The system also includes a controller configured to operate the plurality of sensors. The controller and the heaters of the plurality of sensors are configured to operate a first sensor at a first operating temperature for primary monitoring for flammable compounds, and to operate a second sensor at a second temperature lower than the first temperature and above a temperature at which water vapor condensation can occur.

According to some embodiments, the above air conditioning system refrigerant can have a class 2 or class 2L flammability rating according to ASHRAE 34-2007, Addendum ak, 2010.

According to any one or combination of the above air conditioner system embodiments, the sensors can be disposed in a conduit on the conditioned air flow path comprising an inlet and an outlet, and the first and second sensors are disposed in the conduit with the second sensor downstream from the first sensor with respect to a direction of flow from the inlet to the outlet.

According to some embodiments, a method of operating the air conditioning system according to any one or combination of the above embodiments comprises placing air conditioning system into an operational state that includes flowing the refrigerant on the refrigerant flow path in response to system demand, and periodically or continuously operating the first and second sensors to test for the presence of refrigerant on the conditioned air flow path.

According to any one or combination of the above embodiments, a measured resistance of the first sensor can be compared to a measured resistance of the second sensor.

According to any one or combination of the above embodiments, an operational state of the first sensor can be determined based on the compared resistance measurements of the first and second sensors.

According to any one or combination of the above embodiments, the temperature of the second sensor can be changed to a third temperature that is higher than the second temperature and less than or equal to the first temperature, and the measured resistance of the first sensor compared to the measured resistance of the second sensor at the third temperature.

According to any one or combination of the above embodiments, the third temperature can be from 40° C. to 60° C.

According to any one or combination of the above embodiments, the measured resistance comparison of the first and second sensors can be performed after flowing gas without flammable compounds to the sensors.

According to any one or combination of the above embodiments, the operating temperature of the second sensor can be raised to the first temperature and used for primary monitoring for flammable compounds when the first sensor reaches end of life.

According to any one or combination of the above embodiments, the first temperature can be from 300° C. to 500° C.

According to any one or combination of the above embodiments, the first second temperature can be from 85° C. to 130° C.

According to any one or combination of the above embodiments, a third sensor can be operated at a fourth temperature that is lower than the second temperature and above a temperature at which water vapor condensation can occur.

According to any one or combination of the above embodiments, the third sensor can be disposed in the conduit downstream from the second sensor with respect to the direction of flow from the inlet to the outlet, or the third sensor can be disposed in the conduit isolated from the first and second sensors.

According to any one or combination of the above embodiments, a measured resistance of the first sensor can be compared to a measured resistance of the third sensor.

According to any one or combination of the above embodiments, measured resistance of the first sensor can be compared to measured resistance of the second sensor if the first sensor has detected flammable compounds, and measured resistance of the first sensor can be compared to measured resistance of the third sensor if the first sensor has not detected flammable compounds.

According to any one or combination of the above embodiments, the fourth temperature can be less than or equal to 50° C. and greater than dew point of the gas being monitored.

BRIEF DESCRIPTION OF THE DRAWINGS

Subject matter of this disclosure is particularly pointed out and distinctly claimed in the claims at the conclusion of the specification. The foregoing and other features, and advantages of the present disclosure are apparent from the following detailed description taken in conjunction with the accompanying drawings in which:

DETAILED DESCRIPTION

Figure 1:
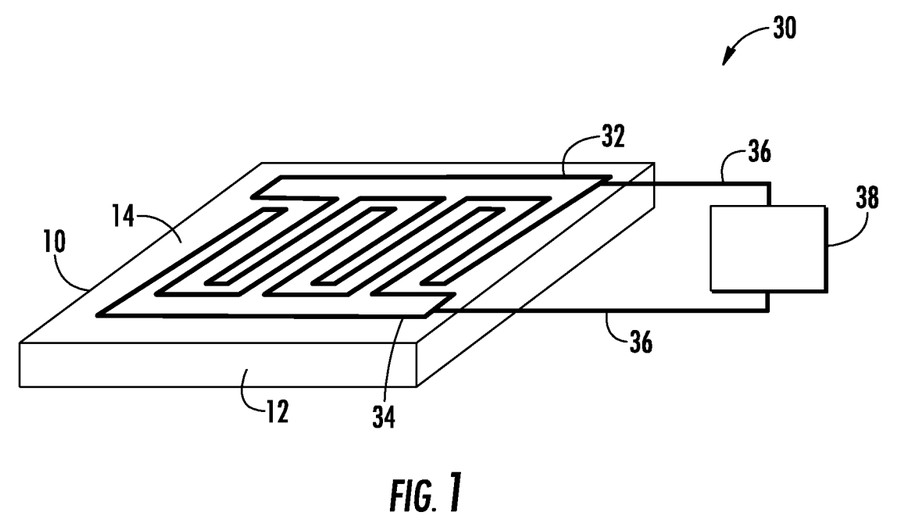
FIG. 1 is a schematic depiction of an example embodiment of a sensor.

As mentioned above, the systems and methods described herein include a plurality of sensors comprising a metal oxide composition. Various types of metal oxide sensor configurations can be used according to this disclosure. In an example embodiment shown in FIG. 1, a gas sensor 30 comprises a gas-sensing element 10 with a metal oxide semiconductor body 12 having a gas-sensing surface 14, integrated with either parallel or interdigitated (as shown, for higher gain) electrodes 32 and 34. The sensor is configured to have doped metal oxide semiconductor at the gas-sensing surface 14 disposed between the interdigitated electrodes 32 and 34. The electrodes 32, 34 are shown on top of the sensing element 10, but can also be disposed in other locations such as at the bottom. The electrodes are connected externally from the gas-sensing element 10 to an electrical circuit 36 that includes a signal processor 38. Signal processor 38 can be a voltmeter or ampere meter, but in many cases comprises a potentiostatic circuit, voltage divider circuit, bridge circuit, microprocessor, electronic control unit (ECU), or similar electronic device with integrated voltage and or amperage measurement functions and also can apply a voltage bias between the electrodes 32 and 34. A heater (not shown) can be in thermally-conductive contact with a surface of the metal oxide semiconductor body 12 (e.g., attached to a bottom surface of the metal oxide semiconductor body 12) and controlled and powered by signal processor 38. Other sensor components including but not limited to housings, mounting hardware, gas flow conduits, fluid chambers are not shown in FIG. 3, but can be incorporated into the sensor by the skilled person.

In some embodiments, metal oxide semiconductor sensors can be configured as an array of sensor elements on an integrated circuit chip. With respect to the plurality of sensors utilized in the methods and systems disclosed herein, the different members of the plurality can be on different chips or on the same chip. For example, sensors operated at different temperatures can be disposed on different chips within the same sensor housing, or on different chips within different sensor housings, in order to facilitate the maintenance of different temperatures. Sensors with different semiconductor compositions can be fabricated on the same chips or on different chips, and can be located in the same sensor housing or different sensor housings. Different members of the plurality of sensors can be mounted in a common location on one circuit board, or can be mounted on different circuit boards, which can be positioned at various locations of interest for gas monitoring.

Examples of metal oxide semiconductors include but are not limited to aluminum (III) oxide, bismuth (III) oxide, cadmium oxide, cerium (IV) oxide, chromium (III) oxide, cobalt (III) oxide, copper (II) oxide, iron (III) oxide, gallium (III) oxide, Indium (III) oxide, molybdenum (VI) oxide, niobium (V) oxide, nickel (II) oxide, tantalum (V) oxide, tin (IV) oxide, titanium (IV) oxide, tungsten (VI) oxide, vanadium (5) oxide, zinc (II) oxide and mixtures of these. Mixed metal oxides (e.g., $SnO_2$—CuO or other mixed oxides of the above metal oxides) can also be utilized. Transition metal dopants can be used to enhance the responsiveness of the metal oxide semiconductor to target gases being sensed for, and to allow for the target gas to be distinguished from other gases that may also produce a change in electrical resistance at the gas-sensing surface 14. In some embodiments, the dopant is a group 5 to group 11 transition metal. Examples of transition metal dopants include copper, silver, gold, iron, ruthenium, nickel, platinum, palladium, or vanadium. Although any of the above materials can exhibit a change in electrical resistance in response to exposure to various test gas components, the use of some materials for particular applications has been more widespread than other materials. For example, copper-doped tin oxide can be used for hydrogen sulfide sensing elements and platinum and palladium doping is commonly used in sensing for hydrogen or hydrocarbons. Such combinations and others are included within this disclosure. Various other materials can be included in the metal oxide semiconductor at the gas-sensing surface 14, including but not limited to noble metals (e.g., silver, gold). Dopants, metal oxide semiconductors, other materials, and combinations thereof are disclosed in Kaur, M. Aswal, D. K. and Yakhmi, J. V." Chemiresistor Gas Sensors: Materials, Mechanisms and Fabrication" Chapter 2 in, *Science and Technology of Chemiresistor Gas Sensors*, Ed. Aswal, D. K. and Gupta, S. K. Nova Science Publishers, New York, 2007., and in Bochenkov, V. E. and Sergeev, G. B. "Sensitivity, Selectivity, and Stability of Gas-Sensitive Metal-Oxide Nanostructures" Chapter 2, in *Metal Oxide Nanostructures and Their Applications*, American Scientific Publishers, California, 2010 the disclosures of each of which is incorporated herein by reference in its entirety.

Figure 2:
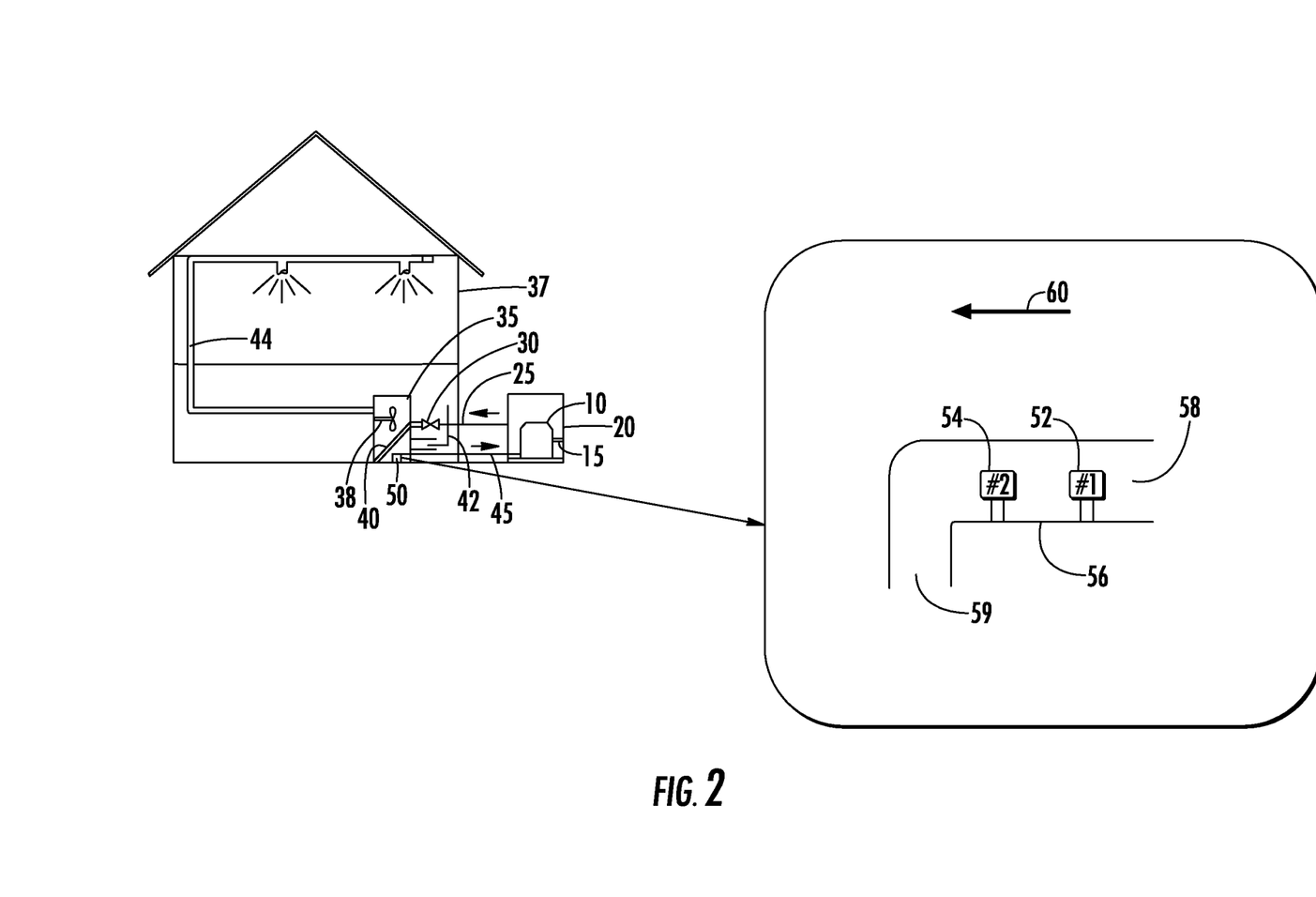
FIG. 2 is a schematic depiction of a system for gas monitoring with two sensors.

As mentioned above, in some embodiments a system for monitoring for flammable or reducing compounds can include at least one sensor operated at a different temperature than another sensor. An example embodiment of a heat transfer system with integrated sensors for monitoring for escaped heat transfer fluid is shown in FIG. 2. As shown in FIG. 2, a heat transfer system includes a compressor 10 which pressurizes the refrigerant or heat transfer fluid in its gaseous state, which both heats the fluid and provides pressure to circulate it throughout the system. The hot pressurized gaseous heat transfer fluid exiting from the compressor 10 flows through conduit 15 to heat rejection heat exchanger 20, which functions as a heat exchanger to transfer heat from the heat transfer fluid to the surrounding environment, resulting in condensation of the hot gaseous heat transfer fluid to a pressurized moderate temperature liquid. The liquid heat transfer fluid exiting from the heat rejection heat exchanger 20 (e.g., a condenser 20) flows through conduit 25 to expansion valve 30, where the pressure is reduced. The reduced pressure liquid heat transfer fluid exiting the expansion valve 30 flows to fan coil unit 35 inside the building 37, which includes fan 38 and heat absorption heat exchanger 40 (e.g., an evaporator), which functions as a heat exchanger to absorb heat from the surrounding environment and boil the heat transfer fluid. In the heat absorption heat exchanger 40, heat is absorbed by the refrigerant from a conditioned air flow path that includes a return air conduit 42 that returns air from the conditioned air space inside the building 37 and a supply air conduit 44 that supplies conditioned air to the conditioned air space inside the building 37. Gaseous heat transfer fluid exiting the heat rejection heat exchanger 40 flows through conduit 45 to the compressor 10, thus completing the heat transfer fluid loop. The heat transfer system can transfer heat from the environment surrounding to the evaporator 40 to the environment surrounding the heat rejection heat exchanger 20. The thermodynamic properties of the heat transfer fluid allow it to reach a high enough temperature when compressed so that it is greater than the environment surrounding the condenser 20, allowing heat to be transferred to the surrounding environment. The thermodynamic properties of the heat transfer fluid should also have a boiling point at its post-expansion pressure that allows the environment surrounding the heat rejection heat exchanger 20 to provide heat at a temperature to vaporize the liquid heat transfer fluid.

As further shown in FIG. 2, the heat transfer system further includes sensor pack 50, which is shown in more detail in the blow-up projection shown in FIG. 2 where sensors 52 and 54 are disposed in a conduit 56 with inlet 58 and outlet 59. The inlet 58 and outlet 59 are open so that the sensors 52 and 54 will be exposed to flammable refrigerant vapor from any leaks. During operation of the fan 38, air moves through the conduit 56 in the direction of arrow 60. In some embodiments, placement of the second sensor 54 downstream of the fir-st sensor 52 can provide a technical effect of the second sensor 54 receiving diluted air in the event of exposure to flammable compounds after activation of the fan from detection by the upstream sensor 52 before the vapor wave front can reach the downstream sensor 54. The sensors are in communication with a controller such as an electronic control unit (ECU, now shown), which can provide power to, direct control of, and receive data from the sensors. In some embodiments, sensor 52 can perform a primary monitoring function and sensor 54 can perform a reference function, diagnostic function, backup monitoring function, or any combination of these functions. Of course, the locations and functions of the described sensors is a particular example embodiment, and other configurations can be used in which any sensor of the plurality of sensors can perform a primary monitoring function, reference function, diagnostic function, backup monitoring function, or any combination of these functions.

As mentioned above, in some embodiments at least one of the plurality of sensors is operated at a different temperature than another of the plurality of sensors. In some embodiments, this can provide a technical effect of allowing one sensor to operate at a higher temperature in a primary monitoring mode, while another sensor operates at a lower temperature at which it can have lower susceptibility to adverse effects such as loss of sensitivity. In some embodiments, the sensor operating at the lower temperature can operate in a secondary monitoring mode, a reference mode, a diagnostic mode, in a backup monitoring mode, or combination of any of these modes, as described in additional detail below.

Figure 3:
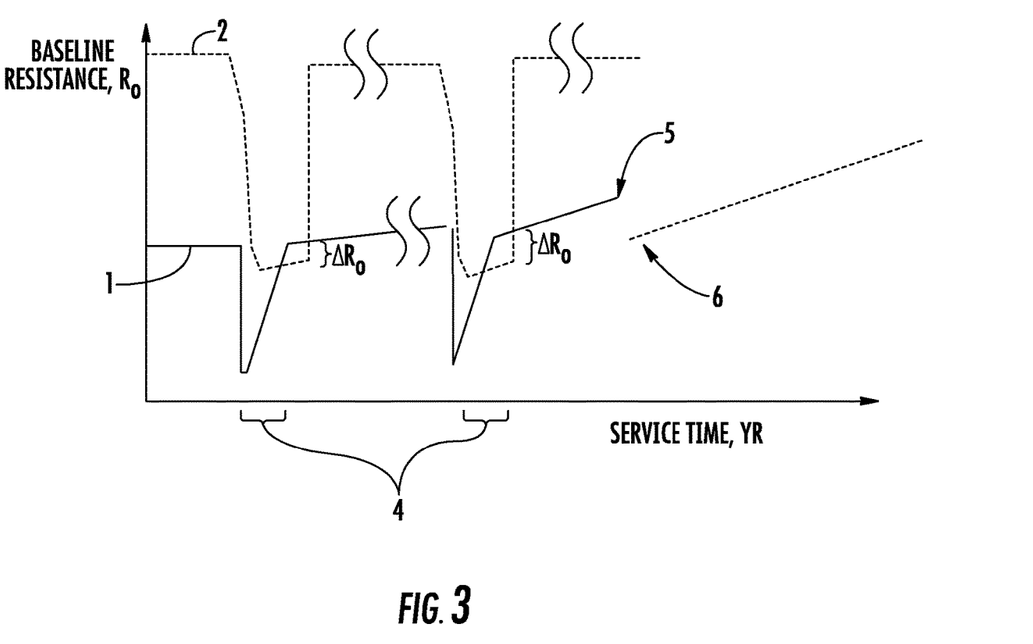
FIG. 3 is a sensor performance plot from an example embodiment of a two-sensor system and method as disclosed herein.

Example embodiments of methods and systems with two sensors operating at different temperatures are described below with respect to FIG. 3. FIG. 3 shows a plot over time of baseline resistance Ro of a first sensor (curve 1) operated at first temperature $T_O$ in a primary monitoring mode. In some embodiments, $T_O$ can be in a range with a lower end of 200° C., 250° C., 275° C., or 300° C., and an upper end of 350° C., 400° C., 450° C., or 500° C. A second sensor (curve 2) is operated at a second temperature $T_P$ that is less than $T_O$. In some embodiments, $T_P$ can be in a range with a lower end of 70° C., 75° C., 80° C., or 85° C., and an upper end of 100° C., 110° C., 120° C., or 130° C. As shown in FIG. 3, at various points in time 4 during the service period, the system can initiate a diagnostic routine, for example in response to an elapsed period of time since the previous diagnostic routine or in response to a detection of flammable compounds by the first sensor 1. As described in more detail below (FIG. 3), the diagnostic can involve flowing clean air to the sensors. The flow of clean air (i.e., no flammable compounds) can be initiated for example by flowing room air along a conditioned air flow path by running fan 38 (FIG. 2) alone, or in the case where monitoring is conducted outside of a system air flow path, a dedicated fan for the sensors (e.g., a fan integrated with conduit 56) can be used. As shown in FIG. 2, the resistance of the first sensor shown in curve 1 initially drops at points 4 from exposure to flammable compound(s) (in this instance it is assumed that the protocol was initiated by a reduction in resistance measured by the first sensor) and then recovers as operation of the fan purges the sensor with clean air. The operating temperature of the second sensor is increased to a temperature approximately equal to $T_O$, resulting in a drop in measured resistance of the second sensor as shown in curve 2. A comparison of the measure resistance of the sensors, designated in FIG. 3 as ΔRo can be made in clean air with the second sensor at its raised temperature, and a state of health of the first sensor can be determined based on the comparison. When ΔRo exceeds a specified value, the first sensor can be retired as shown by the discontinuation of curve 1 at point 5. In some embodiments, the second sensor can then be operated at a new higher temperature $T_O$ as represented by curve 6. During monitoring, the resistance of the sensors can be measured continuously or in repeated pulses, which means that in some embodiments the metal oxide semiconductor composition accommodates some level of continuous or repeated electrical current during monitoring. It should be noted here that the time scale on the x axis of the FIG. 3 plot is not limited to any particular numerical scale, and in some embodiments, monitoring can occur over extended periods, up to and including indefinite periods where monitoring can occur indefinitely until a change of state event such as loss of power, service event, sensor end of life, or occurrence of an alarm condition. In some embodiments, monitoring can extend for up to 10 years.

Figure 4:
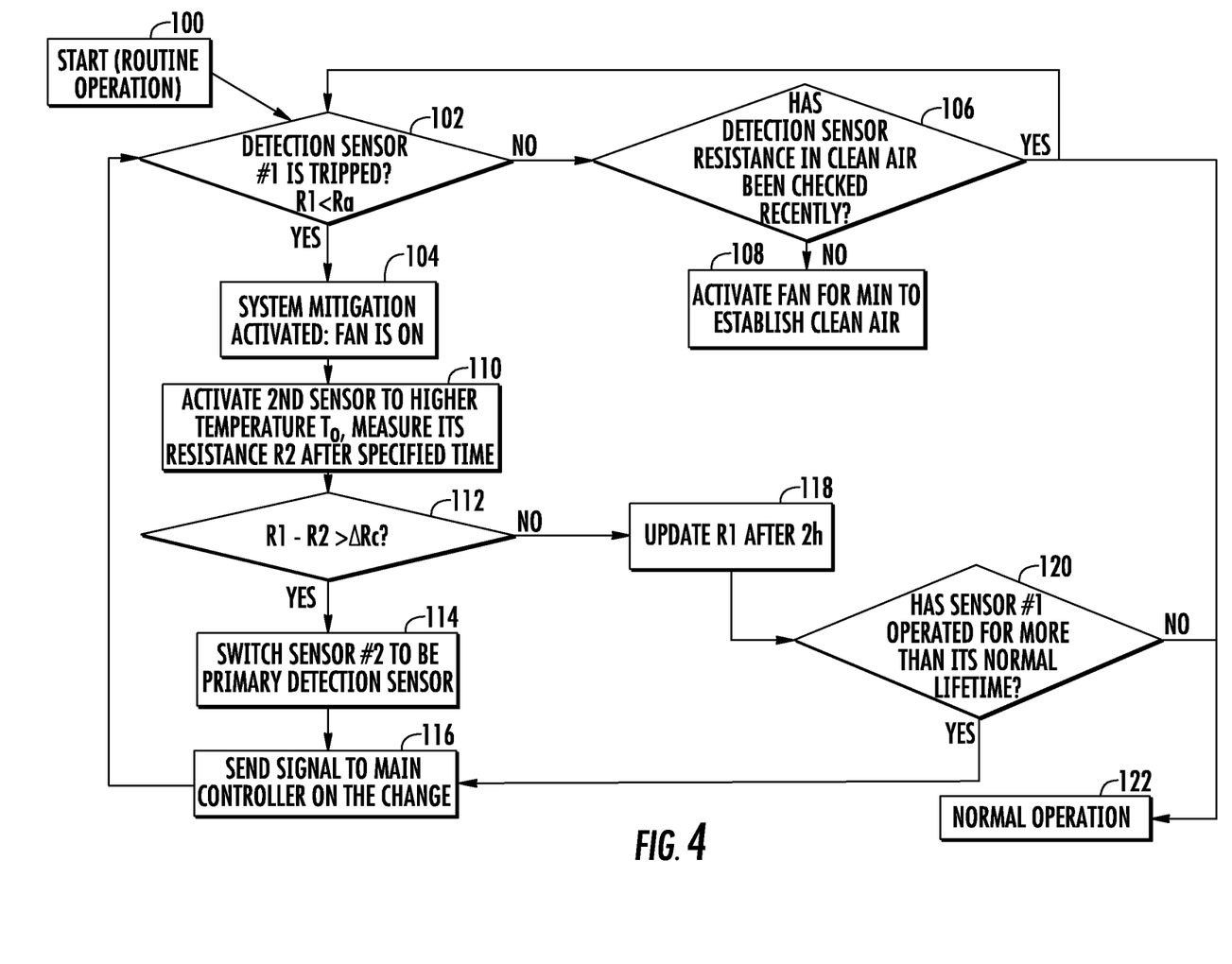
FIG. 4 is a flow chart of an example embodiment of a monitoring protocol for a two-sensor system and method as disclosed herein.

A protocol for conducting the diagnostic routine at points 4 in FIG. 3 is shown in greater detail in FIG. 4. As shown in FIG. 4, initiation of the algorithm routine is represented by block 100, from which the routine proceeds to decision block 102 where a query is performed whether the measured resistance of the first sensor R1 is less than a threshold amount Ra. If R1<Ra, then system mitigation is activated at block 104 by turning on the fan 38 (FIG. 2). If R1 is not less than Ra, then the routine proceeds to decision block 106 where a query is performed whether the first sensor operating as the detection sensor has had resistance checked in a recent defined period (e.g., 1 month). If a recent check has been performed, then the routine can optionally return to decision block 2 for a re-check of whether R1<Ra, or return to normal operation at block 122 if a re-check has already been performed or is not used. If a recent resistance check has not been performed, then the routine proceeds to block 108 where the fan is activated to establish clean air at the sensors. The fan activation at block 108 can be different (e.g., lower fan speed or shorter duration) than the fan activation for system mitigation of flammable vapors undertaken at block 104. In either case, however, the routine proceeds to block 110 in which the second sensor is activated by increasing its temperature to $T_O$ for a predetermined period (e.g., 30 minutes) and measuring its resistance R2. The routine proceeds to decision block 112 where a query is performed whether the difference between R1 and R2 is greater than a specified value ΔRc. If R1−R2>ΔRc, then the routine proceeds to block 114, which initiates a protocol to keep the second sensor's temperature at $T_O$ and operate the second sensor as a new sensor #1. If the difference between R1 and R2 is not greater than ΔRc, then the routine proceeds to block 118 where the R1 measurement is updated, and to decision block 120 where a query is performed whether the first sensor has operated for more than its expected lifespan (e.g., 5 years). If the first sensor has not exceeded its expected lifespan, then the system returns to normal operation at block 122. If the first sensor has exceeded its expected lifespan, the routine proceeds to block 114 for monitoring changeover to the second sensor. At block 116, a signal of this change is sent to the main system controller so that a new sensor #2 can be installed and a new sensor lifetime timer started for the new sensor

1. After installation of the new sensor, the routine returns from block 116 to the decision block 102 for a fresh diagnostic.

Figure 5A:
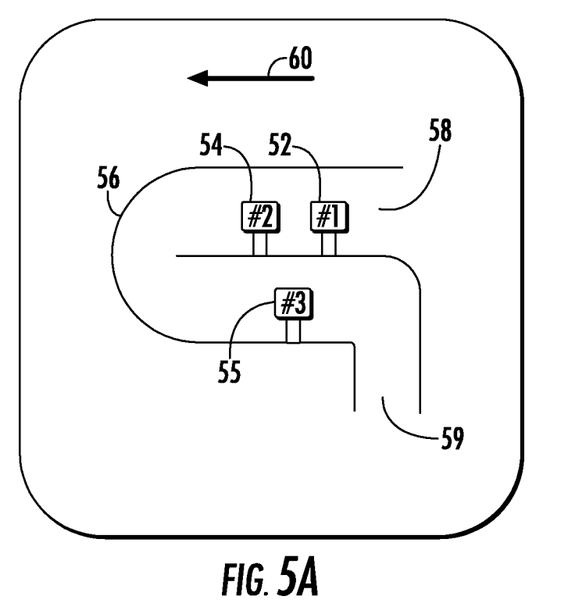
FIGS. 5A and 5B are schematic depictions of first, second, and third sensors disposed in a gas flow conduit.
Figure 5B:
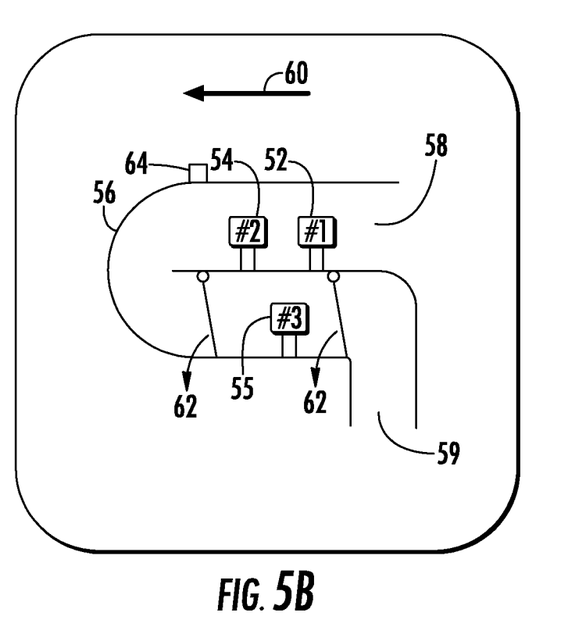
Figure 6:
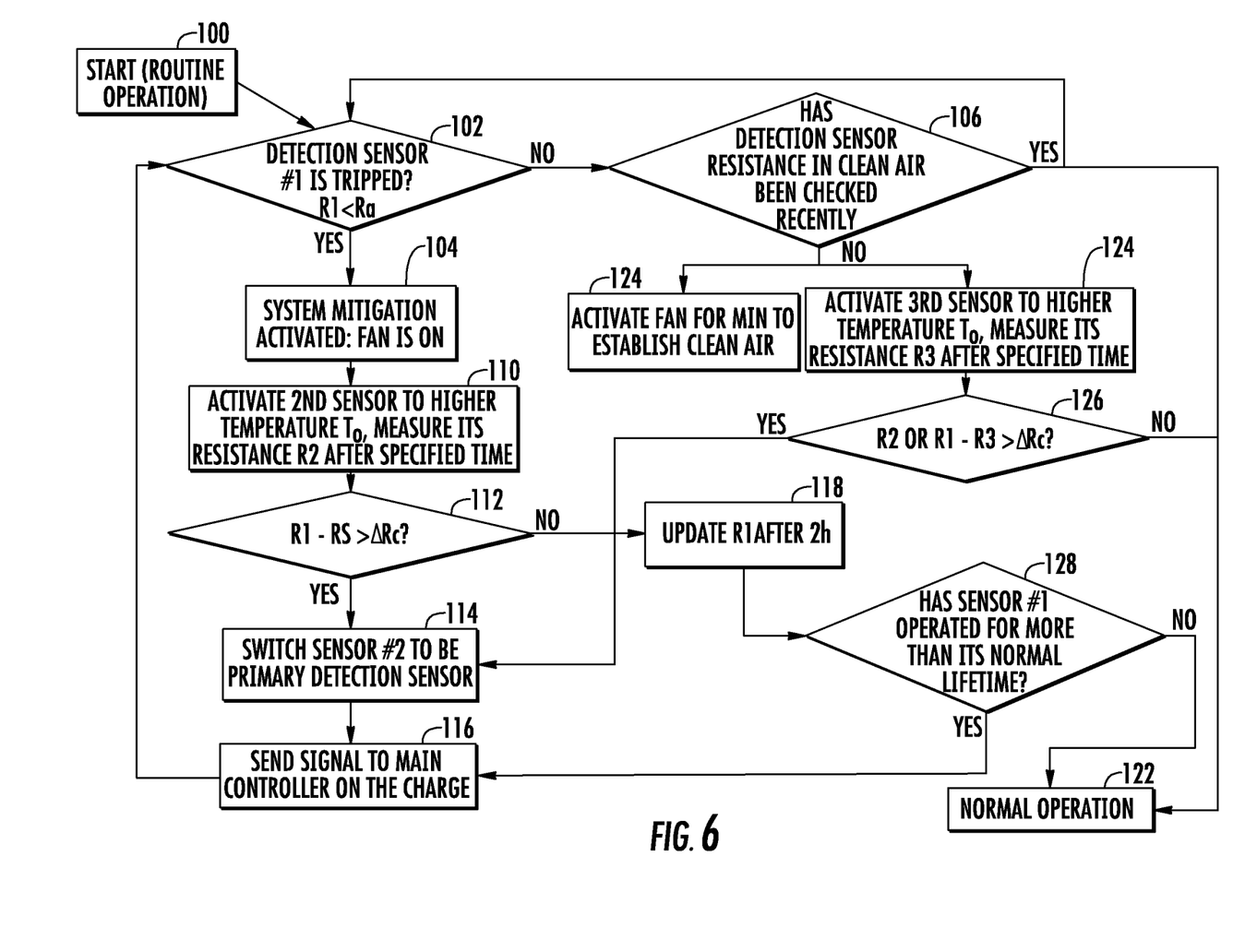
FIG. 6 is a flow chart of an example embodiment of a monitoring protocol for a three-sensor system and method as disclosed herein.

It should be noted that although the above embodiments are described with a single pair of sensors, that multiple pairs configured in the same fashion can be used (e.g., at different locations). Also, sensors can be employed in pluralities of greater than two sensors. For example, in some embodiments, a third sensor can be utilized as shown in FIGS. 5-6. In some embodiments, the third sensor can be operated at a temperature $T_R$ that is less than $T_P$. In some embodiments, $T_R$ can be in a range with a lower end of expected ambient due point (e.g., 32° C., 36° C., or 40° C.), and an upper end of 45° C., 50° C., 55° C., or 60° C. As shown in FIGS. 5A and 5B, a third sensor 55 can be disposed in a conduit 56 for use in a system such as the air conditioning system shown in FIG. 2. FIGS. 5A and 5B use the same component numbering scheme as with the conduit 56 shown in the magnified sensor pack 50 of FIG. 2, which need not be repeated here. As shown in FIG. 5A, the third sensor 55 is separated from the first and second sensors 52/54 by a 180° bend in the conduit. As shown in FIG. 5B, the third sensor 55 is separated from the first and second sensors 52/54 during normal operation by a dampers 62, with vent 64 providing an outlet for gas flow when the outlet 59 is isolated by the dampers 62 in the closed position. In some embodiments, separation or isolation of the third sensor 55 can provide a technical effect of protecting the third sensor from exposure to chemical species that could contaminate the sensor.

A protocol for conducting a diagnostic routine with three sensors is shown in FIG. 6. As shown in FIG. 6, initiation of the algorithm routine is represented by block 100, from which the routine proceeds to decision block 102 where a query is performed whether the measured resistance of the first sensor R1 is less than a threshold amount Ra. If R1<Ra, then system mitigation is activated at block 104 by turning on the fan 38 (FIG. 2). If R1 is not less than Ra, then the routine proceeds to decision block 106 where a query is performed whether the first sensor operating as the detection sensor has had resistance checked in a recent defined period (e.g., 1 month). If a recent check has been performed, then the routine can optionally return to decision block 2 for a re-check of whether R1<Ra, or return to normal operation at block 122 if a re-check has already been performed or is not used. If a recent resistance check has not been performed, then the routine proceeds to blocks 124 where the fan is activated to establish clean air at the sensors, the dampers 62 if present (FIG. 5B) are opened, and the third sensor 55 (FIGS. 5A/5B) is activated by heating to the operating temperature $T_O$ for a period of time (e.g., 30 minutes) and its resistance R3 is measured. The fan activation at block 124 can be different (e.g., lower fan speed or shorter duration) than the fan activation for system mitigation of flammable vapors undertaken at block 104.

In the case of the fan operation at block 104 resulting first sensor being tripped by R1<Ra, the routine proceeds from block 104 to block 110 in which the second sensor is activated by increasing its temperature to $T_O$ for a predetermined period (e.g., 30 minutes) and measuring its resistance R2. The routine then proceeds to decision block 112 where a query is performed whether the difference between R1 and R2 is greater than a specified value ΔRc. If R1−R2>ΔRc, then the routine proceeds to block 114, which initiates a protocol to keep the second sensor's temperature at $T_O$ and operate the second sensor as a new sensor #1, followed by block 116 where a signal of this change is sent to the main system controller so that a new sensor #2 can be installed and a new sensor lifetime timer started for the new sensor #1. After installation of the new sensor, the routine returns from block 116 to the decision block 102 for a fresh diagnostic. If the difference between R1 and R2 is not greater than ΔRc, then the routine proceeds to block 118 where the R1 measurement is updated, and then to decision block 128 where a query is performed where a query is performed whether the first sensor has operated for more than its expected lifespan (e.g., S years). If the first sensor has not exceeded its expected lifespan, then the system returns to normal operation at block 122. If the first sensor has exceeded its expected lifespan, the routine proceeds to block 116 for notification of sensor lifetime expiration to be sent to the system controller. Compared to FIG. 4, this portion of the routine of FIG. 6 represents an alternative embodiment that can be used with two sensors, three sensors, or other numbers of sensors where sensor lifetime expiration results only in notification if the primary sensor otherwise passes the diagnostic routine.

In the case of fan operation and activation of the third sensor 56 at blocks 124 because the first sensor resistance has not been checked recently, the routine proceeds from block 124 to decision block 126 where a query is performed whether R1−R3>ΔRc (or whether R2−R3>ΔRc if the second sensor has previously replaced the first sensor for primary monitoring. If R1 (or R2)−R3>ΔRC, then the routine proceeds to block 114, which initiates a protocol to keep the second sensor's temperature at $T_O$ and operate the second sensor as a new sensor #1. If the difference between R1 (or R2) and R3 is not greater than ΔRC, then the routine proceeds to block 122 for resumption of normal operation.

While the present disclosure has been described in detail in connection with only a limited number of embodiments, it should be readily understood that the present disclosure is not limited to such disclosed embodiments. Rather, the present disclosure can be modified to incorporate any number of variations, alterations, substitutions or equivalent arrangements not heretofore described, but which are commensurate with the spirit and scope of the present disclosure. Additionally, while various embodiments of the present disclosure have been described, it is to be understood that aspects of the present disclosure may include only some of the described embodiments. Accordingly, the present disclosure is not to be seen as limited by the foregoing description, but is only limited by the scope of the appended claims.

The invention claimed is:

1. A method for monitoring for flammable or reducing compounds, comprising measuring metal oxide composition electrical resistance in a plurality of sensors, wherein a first sensor is operated at a first operating temperature as primary monitoring for flammable compounds, and a second sensor is operated at a second temperature lower than the first temperature and above a temperature at which water vapor condensation can occur.

2. A monitoring system for flammable or reducing compounds, comprising
    a plurality of sensors individually comprising a metal oxide semiconductor composition, resistance measurement device, and heater, disposed in communication with a gas being monitored; and
    a controller configured to operate the plurality of sensors; wherein
    the controller and the heaters of the plurality of sensors are configured to operate a first sensor at a first operating temperature for primary monitoring for flammable compounds, and to operate a second sensor at a second temperature lower than the first temperature and above a temperature at which water vapor condensation can occur.

3. The method of claim 1, wherein the gas being monitored is flowing through a conduit, and the first and second sensors are disposed in the conduit with the second sensor downstream from the first sensor with respect to a direction of gas flow through the conduit.

4. An air conditioning system comprising:
a first heat exchanger comprising a conditioned air flow path on a first side of the heat exchanger, and a refrigerant flow path comprising a flammable refrigerant on a second side of the heat exchanger in thermal communication with the first thermal side;
an enclosed fluid flow path comprising the flammable refrigerant connecting the refrigerant flow path of the first heat exchanger with a second heat exchanger in thermal communication with an external heat source or heat sink;
a plurality of sensors individually comprising a metal oxide semiconductor composition, resistance measurement device, and heater, disposed in an air space around the first heat exchanger or the enclosed fluid flow path; and
a controller configured to operate the plurality of sensors; wherein
the controller and the heaters of the plurality of sensors are configured to operate a first sensor at a first operating temperature for primary monitoring for flammable compounds, and to operate a second sensor at a second temperature lower than the first temperature and above a temperature at which water vapor condensation can occur.

5. The system of claim 4, wherein the refrigerant has a class 2 or class 2L flammability rating according to ASHRAE 34-2007, Addendum ak, 2010.

6. The system of claim 4, wherein the sensors are disposed in a conduit on the conditioned air flow path comprising an inlet and an outlet, and the first and second sensors are disposed in the conduit with the second sensor downstream from the first sensor with respect to a direction of flow from the inlet to the outlet.

7. A method of operating the air conditioning system of claim 4, comprising placing air conditioning system into an operational state that includes flowing the refrigerant on the refrigerant flow path in response to system demand, and periodically or continuously operating the first and second sensors to test for the presence of refrigerant on the conditioned air flow path.

8. The method of claim 1, wherein a measured resistance of the first sensor is compared to a measured resistance of the second sensor.

9. The method of claim 8, wherein an operational state of the first sensor is determined based on the compared resistance measurements of the first and second sensors.

10. The method of claim 8, wherein the temperature of the second sensor is changed to a third temperature that is higher than the second temperature and less than or equal to the first temperature, and the measured resistance of the first sensor is compared to the measured resistance of the second sensor at the third temperature.

11. The method of claim 10, wherein the third temperature is from 40° C. to 60° C.

12. The method of claim 7, wherein the measured resistance comparison of the first and second sensors is performed after flowing gas without flammable compounds to the sensors.

13. The method of claim 1, wherein the operating temperature of the second sensor is raised to the first temperature and used for primary monitoring for flammable compounds when the first sensor reaches end of life.

14. The method of claim 1, wherein the first temperature is from 300° C. to 500° C.

15. The method of claim 1, wherein the second temperature is from 85° C. to 130° C.

16. The method of claim 1, wherein a third sensor is operated at a fourth temperature that is lower than the second temperature and above a temperature at which water vapor condensation can occur.

17. The method of claim 3 wherein a third sensor is operated at a fourth temperature that is lower than the second temperature and above a temperature at which water vapor condensation can occur;
wherein the sensors are disposed in a conduit on the conditioned air flow path comprising an inlet and an outlet, and the first and second sensors are disposed in the conduit with the second sensor downstream from the first sensor with respect to a direction of flow from the inlet to the outlet;
wherein the third sensor is disposed in the conduit downstream from the second sensor with respect to the direction of flow from the inlet to the outlet, or wherein the third sensor is disposed in the conduit isolated from the first and second sensors.

18. The method of claim 16, wherein a measured resistance of the first sensor is compared to a measured resistance of the third sensor.

19. The method of claim 8, wherein measured resistance of the first sensor is compared to measured resistance of the second sensor if the first sensor has detected flammable compounds, and measured resistance of the first sensor is compared to measured resistance of the third sensor if the first sensor has not detected flammable compounds.

20. The method of claim 16, wherein the third temperature is less than or equal to 50° C. and greater than dew point of the gas being monitored.

* * * * *